United States Patent
Nakamura et al.

(10) Patent No.: US 10,654,778 B2
(45) Date of Patent: May 19, 2020

(54) METHOD FOR PRODUCING 1-CHLORO-2,3,3-TRIFLUOROPROPENE

(71) Applicant: AGC Inc., Chiyoda-ku (JP)

(72) Inventors: Masahiko Nakamura, Chiyoda-ku (JP); Atsushi Fujimori, Chiyoda-ku (JP); Mari Ichinokawa, Chiyoda-ku (JP); Hidekazu Okamoto, Chiyoda-ku (JP); Hiroaki Mitsuoka, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 0 days.

(21) Appl. No.: 16/425,470

(22) Filed: May 29, 2019

(65) Prior Publication Data

US 2019/0276381 A1 Sep. 12, 2019

Related U.S. Application Data

(63) Continuation of application No. PCT/JP2017/042797, filed on Nov. 29, 2017.

(30) Foreign Application Priority Data

Nov. 30, 2016 (JP) ................................. 2016-232346

(51) Int. Cl.
  *C07C 17/395* (2006.01)
  *C07C 21/18* (2006.01)
(52) U.S. Cl.
  CPC ............ *C07C 17/395* (2013.01); *C07C 21/18* (2013.01)

(58) Field of Classification Search
  CPC .......... C07C 17/16; C07C 17/25; C07C 17/42; C07C 21/18; C07C 19/10; C09K 5/048; C09K 5/04; C07B 61/00
  See application file for complete search history.

(56) References Cited

U.S. PATENT DOCUMENTS

2018/0044268 A1 * 2/2018 Karube ................... C07C 17/16

FOREIGN PATENT DOCUMENTS

| JP | 2016-164152 | 9/2016 |
| WO | WO 94/14737 | 7/1994 |
| WO | WO 2017/018412 A1 | 2/2017 |

OTHER PUBLICATIONS

International Search Report dated Feb. 27, 2018 in PCT/JP2017/042797 filed Nov. 29, 2017 (with English Translation).

* cited by examiner

*Primary Examiner* — Jafar F Parsa
(74) *Attorney, Agent, or Firm* — Oblon, McClelland, Maier & Neustadt, L.L.P.

(57) ABSTRACT

To provide a method for producing 1-chloro-2,3,3-trifluoropropene, whereby it is possible to efficiently remove 1-chloro-3,3-difluoro-1-propyne and/or an oxide from a composition comprising 1-chloro-2,3,3-trifluoropropene. A method for producing 1-chloro-2,3,3-trifluoropropene, in which a composition comprising 1-chloro-2,3,3-trifluoropropene and at least one member selected from 1-chloro-3,3-difluoro-1-propyne and an oxide, is brought into contact with a basic aqueous solution to remove said at least one member selected from 1-chloro-3,3-difluoro-1-propyne and an oxide, from the composition.

11 Claims, No Drawings

METHOD FOR PRODUCING 1-CHLORO-2,3,3-TRIFLUOROPROPENE

TECHNICAL FIELD

The present invention relates to a method for producing 1-chloro-2,3,3-trifluoropropene.

BACKGROUND ART

Hydrochlorofluorocarbons (HCFC) tend to present an adverse effect on the ozone layer, and therefore, it is planned to regulate their production. HCFC are, for example, 3,3-dichloro-1,1,1,2,2-pentafluoropropane (HCFC-225ca), 1,3-dichloro-1,1,2,2,3-pentafluoropropane (HCFC-225cb), etc., but along with the regulation of HCFC, development of a compound in place of HCFC is desired.

An example of the compound in place of HCFC is 1-chloro-2,3,3-trifluoropropene (HClC=CF—CHF$_2$, HCFO-1233yd). HCFO-1233yd is a compound, of which the global warming potential (GWP) is small and which is useful for application to cleaning agents, solvents, refrigerants, blowing agents and aerosols.

Here, Patent Document 1 discloses a method for producing 1,1,2,2,3-pentafluoropropane (HCFC-245ca) by reacting 3-chloro-1,1,2,2-tetrafluoropropane (HCFC-244ca) with hydrogen fluoride in a vapor phase under a nitrogen stream in the presence of chromium hydroxide as a catalyst. In this method, HCFO-1233yd is produced as a by-product. Therefore, by recovering the composition obtained by the above reaction and separating from the composition, it is possible to obtain HCFO-1233yd.

HCFO-1233yd obtained by the above method may be one obtainable as a composition which comprises 1-chloro-3,3-difluoro-1-propyne produced as a by-product in the production step for HCFO-1233yd and an oxide formed by oxidation of HCFO-1233yd by oxygen in air.

At the time of using the above composition containing HCFO-1233yd, as a cleaning agent, solvent, refrigerant, blowing agent or aerosol, if 1-chloro-3,3-difluoro-1-propyne is contained in the composition at a high concentration, it may cause various problems on reliability and performance. In order to suppress such undesirable effects, it is preferred to minimize the content of 1-chloro-3,3-difluoro-1-propyne.

Further, at the time of using the above composition containing HCFO-1233yd in the above application, if the oxide is contained in the composition at a high concentration, it may cause problems such as deterioration of stability and formation of an acidifying agent. In order to suppress such undesirable effects, it is preferred to minimize the content of the oxide.

However, Patent Document 1 fails to disclose a method for effectively removing 1-chloro-3,3-difluoro-1-propyne and the oxide from the composition containing HCFO-1233yd.

PRIOR ART DOCUMENT

Patent Document

Patent Document 1: WO1994/14737

DISCLOSURE OF INVENTION

Technical Problem

The present invention has been made from the above viewpoint and has an object to provide a method for producing 1233yd, whereby it is possible to efficiently remove at least one member selected from 1-chloro-3,3-difluoro-1-propyne and an oxide from a composition comprising 1-chloro-2,3,3-trifluoropropene and said at least one member selected from 1-chloro-3,3-difluoro-1-propyne and an oxide.

Solution to Problem

The method for producing 1-chloro-2,3,3-trifluoropropene (HCFO-1233yd, hereinafter simply referred to also as "1233yd") of the present invention is characterized by contacting a composition comprising 1233yd and at least one member selected from 1-chloro-3,3-difluoro-1-propyne and an oxide, with a basic aqueous solution, to remove said at least one member selected from 1-chloro-3,3-difluoro-1-propyne and an oxide, from the composition.

In the method for producing 1233yd of the present invention, the basic aqueous solution is preferably at least one aqueous solution selected from an alkali metal hydroxide aqueous solution, an alkali metal carbonate aqueous solution, an alkaline earth metal hydroxide aqueous solution, an ammonia aqueous solution and an alkyl ammonium aqueous solution, more preferably at least one aqueous solution selected from a potassium hydroxide aqueous solution and a sodium hydroxide aqueous solution.

Further, in the method for producing 1233yd of the present invention, the temperature for contacting said composition with the basic aqueous solution is preferably from 10° C. to 60° C., and the temperature for contacting said composition with the basic aqueous solution is more preferably from 20° C. to 40° C.

The method for producing 1233yd of the present invention preferably has a step of producing the composition comprising 1233yd and at least one member selected from 1-chloro-3,3-difluoro-1-propyne and an oxide, by subjecting 1-chloro-2,2,3,3-tetrafluoropropane to a dehydrofluorination reaction.

Advantageous Effects of Invention

According to the method for producing 1233yd of the present invention, it is possible to efficiently remove 1-chloro-3,3-difluoro-1-propyne and an oxide from the composition comprising 1233yd and at least one member selected from the 1-chloro-3,3-difluoro-1-propyne and the oxide.

DESCRIPTION OF EMBODIMENTS

In the following, embodiments of the present invention will be described.

First Embodiment

In the method for producing 1233yd according to the first embodiment of the present invention, 1233yd is produced by contacting a composition comprising 1233yd and at least one member selected from 1-chloro-3,3-difluoro-1-propyne and an oxide, with a basic aqueous solution, to let said at least one member selected from 1-chloro-3,3-difluoro-1-propyne and an oxide be dissolved in the basic aqueous solution and removed from the composition.

Hereinafter, "at least one member selected from 1-chloro-3,3-difluoro-1-propyne and an oxide" will be referred to also as the "component to be removed", and the composition comprising 1233yd and the component to be removed, will be referred to also as the "composition to be purified". Here, the component to be removed may be one to be partially or entirely removed.

[Composition to be Purified]

The composition to be purified in this embodiment is not particularly limited, so long as it is a composition comprising 1233yd and at least one member selected from 1-chloro-3,3-difluoro-1-propyne and an oxide. Further, the composition to be purified may contain other components other than 1233yd, 1-chloro-3,3-difluoro-1-propyne and the oxide. Other components may, for example, be HCFC-244ca being an unreacted raw material in the synthesis of 1233yd, by-products other than the 1-chloro-3,3-difluoro-1-propyne and the oxide, formed during the synthesis, water, etc. The composition to be purified may be a liquid or a gas.

As the composition to be purified in this embodiment, it is possible to use, for example, a reaction product containing 1233yd, obtained by reacting various raw materials for the purpose of producing 1233yd. That is, as described later, at the time of the synthesis of 1233yd, if the reaction product contains 1233yd and the component to be removed, by using the reaction product as it is as the composition to be purified, and removing the component to be removed in the composition to be purified, it is possible to obtain highly pure 1233yd. Also, it is possible to use, as the composition to be purified, a composition after removing acidic substances such as hydrogen fluoride, hydrogen chloride, etc. contained in the reaction product by a method such as washing with water.

(1233yd)

1233yd is a fluoroolefin having a double bond between carbon atoms, so that its life in the air is short, and its ozone depletion potential or global warming potential is small.

As 1233yd, depending upon the positions of substituents on the double bond, Z-form and E-form exist as geometrical isomers. In this specification in a case where a compound name or an abbreviation of a compound is used without particularly specified, it represents either one of Z-form, E-form and a mixture of Z-form and E-form, and in a case where (E) or (Z) is indicated after a compound name or an abbreviation of a compound, it represents to be the (E)-form or (Z)-form of the compound. For example, 1233yd (Z) represents the Z-isomer, and 1233yd (E) represents the E-isomer.

The boiling point of 1233yd (Z) is about 54° C., while the boiling point of 1233yd (E) is about 48° C., and both are materials excellent in drying characteristics. Further, even if they are boiled to become vapors, the temperatures of the vapors are at temperatures near the above mentioned respective boiling points, and thus, they are unlikely to present an adverse effect against e.g. resin components susceptible to heat. Further, 1233yd has excellent performance as a cleaning solvent or coating solvent, such that it has no flashpoint, also its surface tension and viscosity are low, and it easily evaporates even at room temperature.

The composition to be purified in this embodiment may contain 1233yd even in a trace amount. The content of 1233yd in the composition to be purified is preferably at least 5 mass %, more preferably at least 10 mass %, further preferably at least 50 mass %, particularly preferably at least 70 mass %, most preferably at least 80 mass %. When the content of 1233yd is at least the above lower limit value, removal efficiency of the component to be removed, will be good. In the composition to be purified in this embodiment, the contents of 1233yd and the component to be removed, are not particularly limited, but from the viewpoint of removal efficiency of the component to be removed, the molar ratio (the component to be removed/1233yd) represented by the content (mol) of the component to be removed to the content (mol) of 1233yd is preferably less than 1, more preferably from 0.1 to 0.7.

1-Chloro-3,3-difluoro-1-propyne

1-Chloro-3,3-difluoro-1-propyne will be formed as the dehydrofluorination reaction of 1233yd represented by the following formula [1] proceeds.

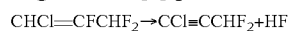

CHCl=CFCHF$_2$→CCl≡CCHF$_2$+HF [1]

In a case where the composition to be purified contains 1-chloro-3,3-difluoro-1-propyne, the content of 1-chloro-3,3-difluoro-1-propyne in the composition to be purified, is, from the viewpoint of removal efficiency, preferably at most 1 mass %, more preferably at most 0.5 mass %, further preferably at most 0.1 mass %.

(Oxide)

The oxide in this embodiment is an oxide formed by a reaction of 1233yd with oxygen. Specifically, 3-chloro-2-(difluoromethyl)-2-fluoro oxirane (chemical formula (A)), 2,2-difluoro-acetyl fluoride (chemical formula (B)), formyl chloride (chemical formula (C)), (E, Z)-1-chloro-2,3,3-trifluoro-1-hydroperoxy-1-propene (chemical formula (D)), 3-chloro-1,1,2-trifluoro-3-hydroperoxy-1-propene (chemical formula (E)), (E, Z)-1-chloro-2,3,3-trifluoro-3-hydroperoxy-1-propene (chemical formula (F)), etc., may be mentioned.

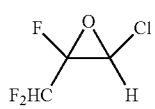
(A)

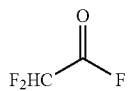
(B)

(C)

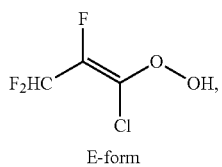 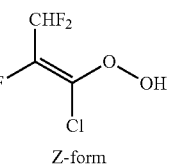
(D)
E-form     Z-form

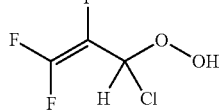
(E)

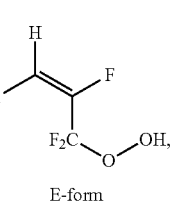 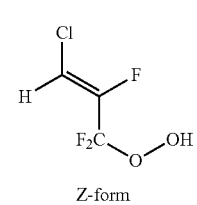
(F)
E-form     Z-form

3-Chloro-2-(difluoromethyl)-2-fluoro oxirane, 2,2-difluoro-acetyl fluoride and formyl chloride may be quantified by conducting the analysis using gas chromatography. The quantification of a hydroperoxide having a —O—O—H structure, such as (E, Z)-1-chloro-2,3,3-trifluoro-1-hydroperoxy-1-propene, 3-chloro-1,1,2-trifluoro-3-hydroperoxy-1-propene or (E, Z)-1-chloro-2,3,3-trifluoro-3-hydroperoxy-1-propene, is conducted by titration with sodium iodide and back-titration with sodium thiosulfate, as represented by the following reaction formulae [2] and [3]. ROOH represents an optional hydroperoxide.

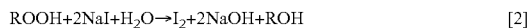  [2]

  [3]

The above titration and back-titration are specifically conducted as follows. To about 50 mL of a sample solution containing the hydroperoxide (ROOH), 2.5 mass % of sodium iodide (NaI) and about 40 mL of an acetone solution are mixed, and about 50 mL of cold water is further added, so that as shown by the above reaction formula [2], the mixed liquid is colored yellow by formed iodine ($I_2$). A case where no coloration takes place at that time, is judged to be such that the hydroperoxide is below the detection lower limit. When colored, the back-titration is conducted with a 0.01 mol/L (0.01 N) sodium thiosulfate ($Na_2S_2O_3$) aqueous solution until the color disappears. The quantitative value of the hydroperoxide is obtained by the following formula by using the experimental values of the above titrations.

Hydroperoxide [mass ppm]={consumed amount [mL] of $Na_2S_2O_3$ aqueous solution×$Na_2S_2O_3$ molar concentration [mol/mL]×(½)×molecular weight of ROOH}/mass [g] of sample solution× $10^6$ In a case where the composition to be purified contains the oxide, the content of the oxide in the composition to be purified is, from the viewpoint of removal efficiency, preferably at most 0.1 mass %, more preferably at most 0.05 mass %, further preferably at most 0.01 mass %.

[Basic Aqueous Solution]

By contacting the composition to be purified in this embodiment with a basic aqueous solution, 1-chloro-3,3-difluoro-1-propyne and the oxide contained in the composition to be purified will be dissolved in the basic aqueous solution and will be transferred to the aqueous phase. Meanwhile, since the basic aqueous solution and 1233yd mutually have only trace amounts of solubility with each other, they form a two-phase system, when the composition to be purified is mixed with the basic aqueous solution. The basic aqueous solution may be an alkali metal hydroxide aqueous solution, an alkali metal carbonate aqueous solution, an alkaline earth metal hydroxide aqueous solution, an ammonia aqueous solution, an alkyl ammonium aqueous solution, etc. As the basic aqueous solution, one type may be used alone, or two or more types may be used in combination.

The basic aqueous solution is, from the viewpoint of removal efficiency of the component to be removed, preferably an alkali metal hydroxide aqueous solution, particularly preferably a potassium hydroxide aqueous solution or a sodium hydroxide aqueous solution. The concentration of the potassium hydroxide aqueous solution or the sodium hydroxide aqueous solution is preferably from 10 mass % to 48 mass %, more preferably from 20 mass % to 40 mass %. When the concentration is in the above range, the difference in specific gravity between the potassium hydroxide aqueous solution or the sodium hydroxide aqueous solution and 1233yd becomes small, whereby the miscibility with the composition to be purified will be improved, and the composition to be purified and the basic aqueous solution tend to readily be in contact with each other.

[Method for Contacting the Basic Aqueous Solution and the Composition to be Purified]

The composition to be purified may be a gas or liquid when it is brought in contact with the basic aqueous solution. In a case where the composition to be purified is brought in contact in a liquid state with the basic aqueous solution, it is possible to make the composition to be purified in a liquid state by adjusting it at a temperature below the boiling points of contained components under normal pressure. Further, the composition to be purified can be made in a liquid state by dissolving it in a solvent. As the solvent to be used in such a case, by using a solvent different in boiling point from 1233yd, it is possible to easily separate the solvent from the composition after purification, by a method such as distillation.

In the method for producing 1233yd in this embodiment, in a case where two or more types of the basic aqueous solution are to be used in combination, the two or more types of the basic aqueous solution may be prepared separately and contacted sequentially to the composition to be purified, or the two or more types of the basic aqueous solution may be mixed to form a mixed solution and contacted simultaneously. In a case where two or more types of the basic aqueous solution are prepared separately and contacted sequentially, the order of the basic aqueous solutions to be contacted is not particularly limited. In such a case, each of the two or more types of the basic aqueous solution may be contacted to the composition to be purified by the later-described method for contacting the composition to be purified with the basic aqueous solution. The contact of these basic aqueous solutions and the composition to be purified, according to such a method, may a batch system (batch) or a continuous system.

In the method for producing 1233yd in this embodiment, the temperature at the time of contacting the composition to be purified with the basic aqueous solution is preferably from 10° C. to 60° C., more preferably from 20° C. to 40° C. When it is at least the above lower limit value, the removal efficiency of the component to be removed will be high, and when it is at most the above upper limit value, it will be possible to suppress side reactions, whereby it is possible to suppress formation of by-products other than 1-chloro-3,3-difluoro-1-propyne and the oxide.

In this embodiment, the contact of the composition to be purified with the basic aqueous solution is preferably carried out in the presence of a phase transfer catalyst. By using a phase transfer catalyst, it is possible to further facilitate the above-described dissolution of 1-chloro-3,3-difluoro-1-propyne and the oxide in the basic aqueous solution. Thus, it is possible to improve the removal efficiency of the component to be removed.

As the phase transfer catalyst, a quaternary ammonium salt, a quaternary phosphonium salt, a quaternary arsonium salt, a sulfonium salt, a crown ether, etc. may be mentioned. Among them, a quaternary ammonium salt is preferred, and tetra-n-butylammonium chloride or tetra-n-butylammonium bromide is more preferred. As the phase transfer catalyst, one type may be used alone, or two or more typed may be used in combination.

Hereinafter, a method of using a liquid composition to be purified will be described. As described above, since 1233yd and the basic aqueous solution have only trace amounts of solubility with each other, when both are mixed together, liquid-liquid two-phases consisting of an organic phase of 1233yd and an aqueous phase of the basic aqueous solution will be formed. Accordingly, in this method, it is preferred to use an apparatus and system capable of sufficiently achieving the contact and mixing of the liquid-liquid two-phases.

For example, in the case of conducting the method for producing 1233yd of this embodiment in a batch system (batch), the composition to be purified and the basic aqueous solution are put into a mixing vessel equipped with a stirrer and an external heating device. In the mixing vessel, liquid-liquid two-phases consisting of the composition to be purified and the aqueous basic solution will be formed, and stirring is conducted sufficiently so that the liquid-liquid two-phases will be well contacted and mixed. Thus, 1-chloro-3,3-difluoro-1-propyne and the oxide will be dissolved in the basic aqueous solution. Thereafter, the stirring is stopped, and the content of the mixing vessel is two-phase separated, whereby it is possible to separate and remove the component to be removed into the basic aqueous solution.

At the time of mixing the composition to be purified and the basic aqueous solution, the internal temperature of the mixing vessel can be maintained at the above-mentioned preferred temperature by the external heating device.

In the method of contacting the basic aqueous solution to the composition to be purified in the mixing vessel containing the basic aqueous solution, the contact time of the composition to be purified and the basic aqueous solution in the mixing vessel, is preferably form 1 hour to 100 hours, more preferably from 3 hours to 60 hours. When the contact time of the composition to be purified and the basic aqueous solution is at least the above lower limit value, the removal efficiency of the component to be removed, will be improved. When the contact time of the composition to be purified and the aqueous basic solution is at most the above upper limit value, it is possible to suppress a side reaction by a reaction of the basic aqueous solution and 1233yd.

Further, in the case of conducting the method for producing 1233yd in this embodiment by a continuous system, the composition to be purified and the basic aqueous solution are continuously supplied to e.g. a mixing vessel equipped with a stirrer and an external heating device and stirred and mixed in the mixing vessel, and thereafter a treated mixed liquid is continuously withdrawn from a withdrawal port provided at another location. At that time, the internal temperature of the mixing vessel can be maintained at the above-mentioned preferred temperature by the external heating device.

In the method of continuously supplying the composition to be purified and the basic aqueous solution into the mixing vessel, the contact time of the composition to be purified and the basic aqueous solution in the mixing vessel is preferably from 1 hour to 100 hours, more preferably from 3 hours to 60 hours. When the contact time of the composition to be purified and the basic aqueous solution is at least the above lower limit value, the removal efficiency of the component to be removed will be improved. When the contact time of the composition to be purified and the basic aqueous solution is at most the above upper limit value, it is possible to suppress a side reaction by a reaction of the basic aqueous solution and 1233yd. Further, in the method of continuously supplying the composition to be purified and the basic aqueous solution into the mixing vessel, the contact time corresponds to the residence time in the mixing vessel of the composition to be purified, and can be controlled by adjusting the supply amount (flow rate) into the mixing vessel of the composition to be purified.

From such a viewpoint that the removal efficiency of the component to be removed will be improved, the total amount of the component to be removed in the composition to be purified, which is to be contacted with the basic aqueous solution, is preferably at most 20 mol %, more preferably at most 10 mol %, to 100 mol % of the total amount of the base contained in the basic aqueous solution. That is, it is preferred to conduct the contact by adjusting the amount of the composition to be purified which is to be contacted with the basic aqueous solution, so that the proportion of the above component to be removed to the base in the basic aqueous solution will be at most the above-mentioned upper limit value.

The material of the mixing vessel to be used for the contact of the composition to be purified and the basic aqueous solution may, for example, be glass, iron, nickel, or an alloy composed mainly of such a material, or a fluororesin such as a tetrafluoroethylene-perfluoro(alkyl vinyl ether) copolymer (PFA). As the mixing vessel to mix and contact the above composition to be purified with the basic aqueous solution, a mixing vessel such as an autoclave capable of contacting the composition to be purified with the basic aqueous solution, in a liquid state at the desired temperature, pressure, etc. may be mentioned.

[Composition after Purification]

In a case where the composition to be purified in this embodiment contains 1-chloro-3,3-difluoro-1-propyne, by contacting the composition to be purified with the above basic aqueous solution, it is possible to dissolve 1-chloro-3,3-difluoro-1-propyne in the basic aqueous solution. This is considered to be such that 1-chloro-3,3-difluoro-1-propyne is converted to be a compound soluble in the basic aqueous solution and thus dissolved. Thus, it is possible to efficiently remove 1-chloro-3,3-difluoro-1-propyne from the composition to be purified and to produce 1233yd.

Further, in a case where the composition to be purified in this embodiment contains an oxide, by contacting the composition to be purified with the basic aqueous solution, it is possible to dissolve the oxide in the basic aqueous solution. This is considered to be such that the oxide is converted to a compound soluble in the basic aqueous solution and thus dissolved. Thus, it is possible to efficiently remove the oxide from the composition to be purified and to produce 1233yd.

The content of 1233yd in the composition obtained by the method for producing 1233yd in this embodiment is preferably at least 90 mass %, more preferably at least 95 mass %, further preferably at least 99 mass %. The content of 1-chloro-3,3-difluoro-1-propyne in the composition after purification is preferably at most 100 mass ppm, and the content of the oxide is preferably at most 12 mass ppm, more preferably at most 10 mass ppm, further preferably at most 5 ppm by mass. When the content of the oxide is at most the above upper limit value, it is possible to sufficiently prevent the deterioration of the stability of the composition. Further, when the content of oxide is at most the above upper limit value, it may not be reduced to the limit of 0 mass ppm. The content of the oxide in the composition after purification, is preferably at least 1 mass ppm, more preferably at least 2 mass ppm. When it is at least the above lower limit value, oxidation of 1233yd will be suppressed, and the stability of the composition will be excellent.

Second Embodiment

The method for producing 1233yd as the second embodiment of this invention has a step of producing a composition to be purified containing 1233yd by e.g. a method of the following (I) or (II).

(I) A method of reacting HCFC-244ca with hydrogen fluoride in a vapor phase in a nitrogen stream by using chromium oxide as a catalyst.

(II) A method of subjecting HCFC-244ca to a dehydrofluorination reaction at a temperature of from 40° C. to 80° C. by using potassium hydroxide or sodium hydroxide as a reactant.

In the method for producing 1233yd in this embodiment, by applying the purification as described in the above first embodiment to e.g. the reaction product obtainable by the synthesis of 1233yd as shown in the above (I) or (II) or to a mixed composition obtained by removing acidic substances, etc. from the reaction product, it is possible to efficiently remove at least one member selected from 1-chloro-3,3-difluoro-1-propyne and the oxide from the composition comprising 1233yd and said at least one member selected from 1-chloro-3,3-difluoro-1-propyne and the oxide.

(I) A Method of Reacting HCFC-244Ca with Hydrogen Fluoride in a Vapor Phase in a Nitrogen Stream by Using Chromium Oxide as a Catalyst A raw material composition comprising HCFC-244ca and hydrogen fluoride is reacted in a vapor phase in a reaction vessel having a catalyst layer packed with a chromium oxide catalyst to produce HCFC-245ca and at the same time to form a composition containing 1233yd which is by-produced.

In such a vapor phase catalytic reaction of HCFC-244ca with hydrogen fluoride, it is possible to obtain a reaction product comprising 1233yd and acidic substances such as hydrogen chloride, etc. as the outlet gas of the reaction vessel. Then, by removing the acidic substances such as hydrogen fluoride, hydrogen chloride, etc. contained in the reaction product, it is possible to obtain a mixed composition. Compounds other than 1233yd contained in the mixed composition may be, other than HCFC-244ca as unreacted raw material, water, 1-chloro-3,3-difluoro-1-propyne, HCFC-245ca, 2,3,3-trifluoropropene ($H_2C=CF-CHF_2$), 1,2,3,3-tetrafluoropropene ($HFC=CF-CHF_2$), an oxide, etc.

By applying the method of producing 1233yd according to the first embodiment to such a reaction product or mixed composition thus obtained, it is possible to efficiently remove at least part of the component to be removed, from the composition comprising 1233yd and at least one member selected from 1-chloro-3,3-difluoro-1-propyne and the oxide. Other components (such as water, etc.) other than 1233yd which are contained in the reaction product or mixed composition, and will be contained in the composition after purification, may be removed to a desired extent by a known means such as distillation.

(II) A Method of Subjecting HCFC-244Ca to a Dehydrofluorination Reaction at a Temperature of from 40° C. to 80° C. by Using Potassium Hydroxide or Sodium Hydroxide as a Reactant By subjecting HCFC-244ca to a dehydrofluorination reaction at a temperature of from 40° C. to 80° C. in a potassium hydroxide aqueous solution or a sodium hydroxide aqueous solution, a composition containing 1233yd is formed. In the above reaction, it is preferred to conduct the dehydrofluorination reaction in the presence of a phase transfer catalyst for the purpose of accelerating the reaction. Further, the amount of potassium hydroxide or sodium hydroxide in the potassium hydroxide or sodium hydroxide aqueous solution is preferably from 1 to 3-fold molar amount to the molar amount of HCFC-244ca.

In such a synthesis method of subjecting HCFC-244ca to a dehydrofluorination reaction in a potassium hydroxide or sodium hydroxide aqueous solution, by separating the reaction liquid after completion of the reaction into an organic phase and an aqueous phase, it is possible to obtain, as the organic phase, a reaction product containing 1233yd. Compounds other than 1233yd contained in the reaction product may, for example, be, in addition to HCFC-244ca as an unreacted raw material, water, 1-chloro-3,3-difluoro-1-propyne, an oxide, etc. By applying the method for producing 1233yd according to the first embodiment, to the obtained reaction product, it is possible to efficiently remove the component to be removed.

Further, according to the method of the above (II), to the reaction product obtained, i.e. to the mixed composition comprising 1233yd and a component to be removed, it is possible to apply the method for producing 1233yd according to the first embodiment continuously. Thus, it is thereby possible to efficiently remove the component to be removed from the mixed composition. For example, in a case where the above dehydrofluorination reaction of HCFC-244ca has been carried out at from 40° C. to 80° C. in a potassium hydroxide or sodium hydroxide aqueous solution, after completion of the reaction, by maintaining the temperature of the reaction liquid at from 20° C. to 40° C., it is possible to efficiently remove 1-chloro-3,3-difluoro-1-propyne and the oxide. Thereafter, by separating the reaction liquid into an organic phase and an aqueous phase, it is possible to obtain 1233yd having reduced the component to be removed in the organic phase. Other components (such as water, etc.) other than 1233yd contained in the reaction product after purification, can be removed to a desired extent by a known means such as distillation.

EXAMPLES

In the following, the present invention will be described with reference to Examples, but the present invention is by no means limited by these Examples.

(Analysis Method)

The composition other than hydroperoxide in the composition to be analyzed, is analyzed by gas chromatography having a flame ionization detector (FID detector). As the column, DB-1301 (length 60 m×inside diameter 250 μm×thickness 1 μm, manufactured by Agilent Technologies Co., Ltd.) is used. The amount of each component contained in the composition to be analyzed is obtained as GCArea %. Here, GCArea % is the proportion of the peak area derived from the particular component to the total area of all peaks detected by the flame ionization detector. The content of hydroperoxide in the composition to be analyzed was determined by the above-described hydroperoxide measuring method.

Synthesis Example: Synthesis of 1233yd

Using 2,000 g of HCFC-244ca as raw material, 19.9 g of tetra-n-butylammonium chloride was put, and while maintaining the reaction temperature at 50° C., 2,792 g of a 40 mass % potassium hydroxide aqueous solution was dropwise added over 30 minutes. Thereafter, the reaction was continued for 52 hours, whereupon an organic phase and an aqueous phase were separated for two phase separation, and the organic phase was recovered. The recovered organic phase was roughly distilled by batch distillation, and the distillate fractions were recovered to obtain a composition (composition to be purified) comprising 1233yd, 1-chloro- 3,3-difluoro-1-propyne and oxides. Here, in the initial distillate of the batch distillation, 1-chloro-3,3-difluoro-1-propyne is contained in a large amount, and on the other hand, in the later distillate, the oxides are contained in a large amount.

Example 1

The amounts of oxides contained in the composition to be purified, obtained by the above Synthesis Example were quantified by the above-mentioned gas chromatography and hydroperoxide measuring method, whereby 3-chloro-2-(difluoromethyl)-2-fluoro oxirane was 20 mass ppm, and hydroperoxide was 19 mass ppm, i.e. the total being 39 mass ppm. 1 kg of the composition to be purified, containing the above oxides, was put in a 2 L four-necked flask provided with a stirrer and a Dimroth condenser, and taking the 1 kg of the composition to be purified as 100 mass %, 1 mass % relative thereto of tetra-n-butylammonium bromide and 1 kg of a 20 mass % potassium hydroxide aqueous solution were added, followed by stirring at room temperature (25° C.) for about 60 hours.

After completion of the stirring, the organic phase and the aqueous phase were left to stand still for two phase separation, whereupon the organic phase was recovered. The contents of oxides in the recovered organic phase were measured, whereby 3-chloro-2-(difluoromethyl)-2-fluoro oxirane was 0 mass ppm, and hydroperoxide was 0.1 mass ppm. Thus, it is evident that by contacting the composition comprising 1233yd and the oxides, with the potassium hydroxide aqueous solution, it is possible to remove the oxides contained in the above composition.

Example 2

With respect to the composition to be purified, obtained by the above Synthesis Example, the composition analysis was conducted by gas chromatography provided with a flame ionization detector, whereby 1233yd and 1-chloro-3,3-difluoro-1-propyne were contained with the composition as shown in Table 1. 1 g of the composition to be purified having the composition ratio as shown in Table 1, was put into a 20 ml sample bottle provided with a polytetrafluoroethylene (PTFE) stirrer, and tetra-n-butylammonium bromide at a concentration of 1 mass % to 1 g of the composition to be purified and 1 g of a 20 mass % potassium hydroxide aqueous solution were added, followed by stirring at room temperature (25° C.) for about 60 hours. After completion of the stirring, the organic phase and the aqueous phase were left to stand still for two phase separation, whereupon the organic phase was recovered. With respect to the recovered organic phase, the composition analysis was conducted by gas chromatography provided with a flame ionization detector, whereby the composition was as shown in Table 1.

Example 3

The amounts of oxides contained in the composition to be purified, obtained by the above Synthesis Example were quantified by the above-mentioned gas chromatography and hydroperoxide measurement, whereby 3-chloro-2-(difluoromethyl)-2-fluoro oxirane was 20 mass ppm, and hydroperoxide was 19 mass ppm, i.e. the total being 39 mass ppm. 1 kg of the composition to be purified, containing the above oxides, was put into a 2 L four-necked flask provided with a stirrer and a Dimroth condenser, and tetra-n-butylammonium bromide at a concentration of 1 mass % to 1 kg of the composition to be purified, and 1 kg of a 20 mass % potassium hydroxide aqueous solution were added, followed by stirring at 10° C. for about 60 hours. After completion of the stirring, the organic phase and the aqueous phases were left to stand still for two phase separation, whereupon the organic phase was recovered. The amounts of oxides in the recovered organic layer were measured, whereby 3-chloro-2-(difluoromethyl)-2-fluoro oxirane was 0 mass ppm, and hydroperoxide was 10.2 mass ppm.

Example 4

With respect to the composition to be purified, obtained by the above Synthesis Example, the composition analysis was conducted by gas chromatography provided with a flame ionization detector, whereby 1233yd and 1-chloro-3,3-difluoro-1-propyne were contained with the composition as shown in Table 1. 1 g of the composition to be purified having the composition ratio as shown in Table 1, was put into a 20 ml sample bottle provided with a PTFE stirrer, and tetra-n-butylammonium bromide at a concentration of 1 mass % to 1 g of the composition to be purified, and 1 g of a 20 mass % potassium hydroxide aqueous solution were added, followed by stirring at 10° C. for about 60 hours. After completion of the stirring, the organic phase and the aqueous phases were left to stand still for two phase separation, whereupon the organic phase was recovered. With respect to the recovered organic phase, the composition analysis was conducted by gas chromatography provided with a flame ionization detector, whereby the composition was as shown in Table 1.

Example 5

The amounts of oxides contained in the composition to be purified, obtained by the above Synthesis Example were quantified by the above-mentioned gas chromatography and hydroperoxide measurement, whereby 3-chloro-2-(difluoromethyl)-2-fluoro oxirane was 20 mass ppm, and hydroperoxide was 19 mass ppm, i.e. the total being 39 mass ppm. 1 kg of the composition to be purified containing the above oxides, was put into a 2 L four-necked flask provided with a stirrer and a Dimroth condenser, and tetra-n-butylammonium bromide at a concentration of 1 mass % to 1 kg of the composition to be purified, and 1 kg of a 20 mass % potassium hydroxide aqueous solution were added, followed by stirring at 50° C. for about 60 hours. After completion of the stirring, the organic phase and the aqueous phase were left to stand for two phase separation, whereupon the organic layer was recovered. The amounts of the oxides in the recovered organic layer were measured, whereby 3-chloro-2-(difluoromethyl)-2-fluoro oxirane was 0 mass ppm, and hydroperoxide was 0.1 mass ppm.

Example 6

With respect to the composition to be purified, obtained by the above Synthesis Example, the composition analysis was conducted by gas chromatography provided with a flame ionization detector, whereby 1233yd and 1-chloro-3,3-difluoro-1-propyne were contained with the composition as shown in Table 1. 1 g of the composition to be purified having the composition ratio as shown in Table 1, was put into a 20 ml sample bottle provided with a PTFE stirrer, and tetra-n-butylammonium bromide at a concentration of 1 mass % to 1 g of the composition to be purified, and 1 g of a 20 mass % potassium hydroxide aqueous solution were added, followed by stirring at 50° C. for about 60 hours. After completion of the stirring, the organic phase and the aqueous phase were left to stand still for two phase separation, whereupon the organic layer was recovered. With respect to the recovered organic layer, the composition analysis was conducted by gas chromatography provided with a flame ionization detector, whereby the composition was as shown in Table 1.

TABLE 1

| Abbreviations of compounds, etc. | Unit | Composition before treatment | Example 2 | Example 4 | Example 6 |
|---|---|---|---|---|---|
| 1233yd(Z) | GCArea % | 0.1 | 0.1 | 0.1 | 0.0 |
| 1233yd(E) | GCArea % | 86.8 | 95.3 | 88.5 | 94.7 |
| HCFC-244ca | GCArea % | 0.1 | 0.0 | 0.1 | 0.0 |
| 1-chloro-3,3-difluoro-1-propyne | GCArea % | 12.1 | 3.4 | 10.4 | 1.5 |
| Others | GCArea % | 1.0 | 1.2 | 1.0 | 3.9 |
| Total (components detected by gas chromatography) | GCArea % | 100.0 | 100.0 | 100.0 | 100.0 |
| Time for contact with basic aqueous solution | | — | 60 hrs | 60 hrs | 60 hrs |
| Temperature for contact with basic aqueous solution | | — | Room temperature | 10° C. | 50° C. |

From the above Examples, it is evident that by contacting the composition comprising 1233yd and at least one member of 1-chloro-3,3-difluoro-1-propyne and an oxide, with a potassium hydroxide aqueous solution, it is possible to remove said at least one member of 1-chloro-3,3-difluoro-1-propyne and an oxide contained in the composition.

This application is a continuation of PCT Application No. PCT/JP2017/042797, filed on Nov. 29, 2017, which is based upon and claims the benefit of priority from Japanese Patent Application No. 2016-232346 filed on Nov. 30, 2016. The contents of those applications are incorporated herein by reference in their entireties.

What is claimed is:

1. A method for producing 1-chloro-2,3,3-trifluoropropene, comprising:
   contacting a composition comprising 1-chloro-2,3,3-trifluoropropene and at least one member selected from the group consisting of 1-chloro-3,3-difluoro-1-propyne and an oxide, with a basic aqueous solution at a temperature of from 20° C. to 40° C., thereby removing the at least one member from the composition,
   wherein a content of the 1-chloro-2,3,3-trifluoropropene in the composition is at least 80 mass %.

2. The method according to claim 1, wherein the basic aqueous solution is at least one member selected from the group consisting of an alkali metal hydroxide aqueous solution, an alkali metal carbonate aqueous solution, an alkaline earth metal hydroxide aqueous solution, an ammonia aqueous solution and an alkyl ammonium aqueous solution.

3. The method according to claim 1, wherein the basic aqueous solution is at least one member selected from the group consisting of a potassium hydroxide aqueous solution and a sodium hydroxide aqueous solution.

4. The method according to claim 1, wherein the composition is contacted with the basic aqueous solution for 1 hour to 100 hours.

5. The method according to claim 4, wherein the composition is contacted with the basic aqueous solution for 3 hours to 60 hours.

6. The method according to claim 1, further comprising, prior to the contacting:
   producing the composition by subjecting 1-chloro-2,2,3,3-tetrafluoropropane to a dehydrofluorination reaction.

7. The method according to claim 1, wherein the oxide is at least one member selected from the group consisting of 3-chloro-2-(difluoromethyl)-2-fluoro oxirane, 2,2-difluoroacetyl fluoride, formyl chloride, E-form of 1-chloro-2,3,3-trifluoro-1-hydroperoxy-1-propene, Z-form of 1-chloro-2,3,3-trifluoro-1-hydroperoxy-1-propene, 3-chloro-1,1,2-trifluoro-3-hydroperoxy-1-propene, E-form of 1-chloro-2,3,3-trifluoro-3-hydroperoxy-1-propene, and Z-form of 1-chloro-2,3,3-trifluoro-3-hydroperoxy-1-propene.

8. A method for producing 1-chloro-2,3,3-trifluoropropene, comprising:
   contacting a composition comprising 1-chloro-2,3,3-trifluoropropene and an oxide with a basic aqueous solution, thereby removing the oxide from the composition,
   wherein the oxide is at least one member selected from the group consisting of 3-chloro-2-(difluoromethyl)-2-fluoro oxirane, 2,2-difluoro-acetyl fluoride, formyl chloride, E-form of 1-chloro-2,3,3-trifluoro-1-hydroperoxy-1-propene, Z-form of 1-chloro-2,3,3-trifluoro-1-hydroperoxy-1-propene, 3-chloro-1,1,2-trifluoro-3-hydroperoxy-1-propene, E-form of 1-chloro-2,3,3-trifluoro-3-hydroperoxy-1-propene, and Z-form of 1-chloro-2,3,3-trifluoro-3-hydroperoxy-1-propene.

9. The method according to claim 1, wherein the contacting is performed in the presence of a phase transfer catalyst.

10. The method according to claim 9, wherein the phase transfer catalyst comprises a quaternary ammonium salt.

11. The method according to claim 1, wherein a molar ratio of a content of the at least one member to a content of the 1-chloro-2,3,3-trifluoropropene in the composition is 0.1 to 0.7.

* * * * *